United States Patent
Katsev

Patent Number: 5,861,001
Date of Patent: Jan. 19, 1999

[54] ORTHOPEDIC NASAL AIRWAY APPLIANCE

[76] Inventor: Robert Katsev, #5 Crossbow, Overland, Mo. 63114

[21] Appl. No.: 803,629

[22] Filed: Feb. 21, 1997

[51] Int. Cl.[6] ........................................... A61F 5/08
[52] U.S. Cl. ........................................... 606/204.45; 433/7
[58] Field of Search .................. 606/204.45; 433/7, 433/6, 18

[56] References Cited

U.S. PATENT DOCUMENTS

| | | | |
|---|---|---|---|
| 4,170,230 | 10/1979 | Nelson | 128/139 |
| 4,261,354 | 4/1981 | Nelson | 128/203.23 |
| 4,262,666 | 4/1981 | Nelson | 128/203.23 |
| 4,275,725 | 6/1981 | Nelson | 128/207.14 |
| 4,289,127 | 9/1981 | Nelson | 128/207.14 |
| 4,416,626 | 11/1983 | Bellavia | 433/7 |
| 4,431,411 | 2/1984 | Witzig et al. | 433/6 |
| 4,433,956 | 2/1984 | Witzig | 433/7 |
| 4,439,148 | 3/1984 | Hass | 433/5 |
| 4,554,549 | 11/1985 | Pope et al. | 128/421 |
| 4,573,914 | 3/1986 | Nord | 433/7 |
| 4,715,368 | 12/1987 | George | 128/136 |
| 4,723,910 | 2/1988 | Keller | 433/7 |
| 4,797,093 | 1/1989 | Bergersen | 433/7 |
| 4,815,968 | 3/1989 | Keller | 433/7 |
| 4,901,737 | 2/1990 | Toone | 128/848 |
| 5,003,994 | 4/1991 | Cook | 128/848 |
| 5,052,409 | 10/1991 | Tepper | 128/859 |
| 5,147,358 | 9/1992 | Remmler | 606/57 |

OTHER PUBLICATIONS

Katsev, *Journal of AAGO*, vol. 6 No. 4 (1989).
Katsev, *Journal of AAGO*, vol. 10 No. 4 (1993).
Meredith, *Journal of AAGO*, vol 12 No. 3 (1995).

*Primary Examiner*—Michael Buiz
*Assistant Examiner*—Kevin Truong
*Attorney, Agent, or Firm*—Dennis A. Bennett

[57] ABSTRACT

Disclosed is a novel orthopedic device for opening a patient's nasal airway.

7 Claims, 1 Drawing Sheet

ORTHOPEDIC NASAL AIRWAY APPLIANCE

BACKGROUND OF THE INVENTION

1. Field of the Invention

This invention relates to an orthopedic appliance for controlled loading of the maxillas, more particularly to a nasal airway device which can be used to shape and/or open nasal airways.

2. Related Art

The art illustrates that there is an interrelationship between airway obstruction and abnormal dentofacial development.

Patients with chronic interference with nasal airflow, Panorax's, A-P's, P-A's and CAT scans commonly show misshapen posterior end of the inferior turbonates, deviated sepia, and distorted sinuses. Some patients are "obligatory" mouth-breathers; others report persistent unilateral nasal airway, and a few have postnasal drip. The patients usually relate histories of chronic or recurrent sinus problems. Nasal surgery alone is unlikely to produce optimum results if relationships of bony structures are abnormal. Dental orthopedics can give improvement, if not a solution to all these airway problems and can be adjusted to the exact requirements of each patient until ideal results are achieved.

SUMMARY OF THE INVENTION

The present invention provides an appliance to open nasal airway in a controlled manner without the need for surgery and/or medications.

The present invention offers the following objectives and/or advantages:

1. Opens nasal airway without surgery.
2. Little or no effect on speech.
3. Very controlled.
4. Safe, all effects reversible.
5. Expands maxilla to aid in opening airways.
6. Torque's frontal process of maxilla wider to free-up lower turbonates and open maxillary sinus.
7. Can avoid opening airway too much, hence can shape to perfection, can even change for climate and seasons or when you have a cold.
8. Device will, in general, still go in place if left out for long periods.
9. Is very gentle to cranial structure. Seldom causing pain or cranial distress, in fact, will release cranial distortions.
10. Eliminate sinus headaches and congestion even in frontal sinus.
11. Transfers the expansion and torque loads into the entire length of the posterior teeth by the way it encapsulates the crowns of the teeth.
12. Can be used as night retainer.
13. Can double as splint on nonbruxing and/or non-clenching patients.
14. Counters sleep posture loads on the face.
15. The dentist can work in concert with the physician to achieve the most balanced and open shape of both sides of nasal airway.
16. Can be removed to eat or clean.
17. In cases where medication can be a risk, congested sinuses can be opened without using medication.
18. Reduce or eliminate need for decongestants and their side effects.
19. Reduce or eliminate need for antibiotices in sinus infections.
20. Improve sense of smell.
21. Stop or reduce snoring.
22. Stop or reduce sleep apnea.
23. In conjunction with lower device, a hawley with anterior contact can protect vertical, TMJ, and advance mandible.

IN THE DRAWINGS

FIG. 1 is a diagrammatic perspective view of the orthopedic appliance of the present invention with an optional posterior wire seated in the upper mouth of a patient.

DETAILED DESCRIPTION OF THE PRESENT INVENTION

Figure 1:
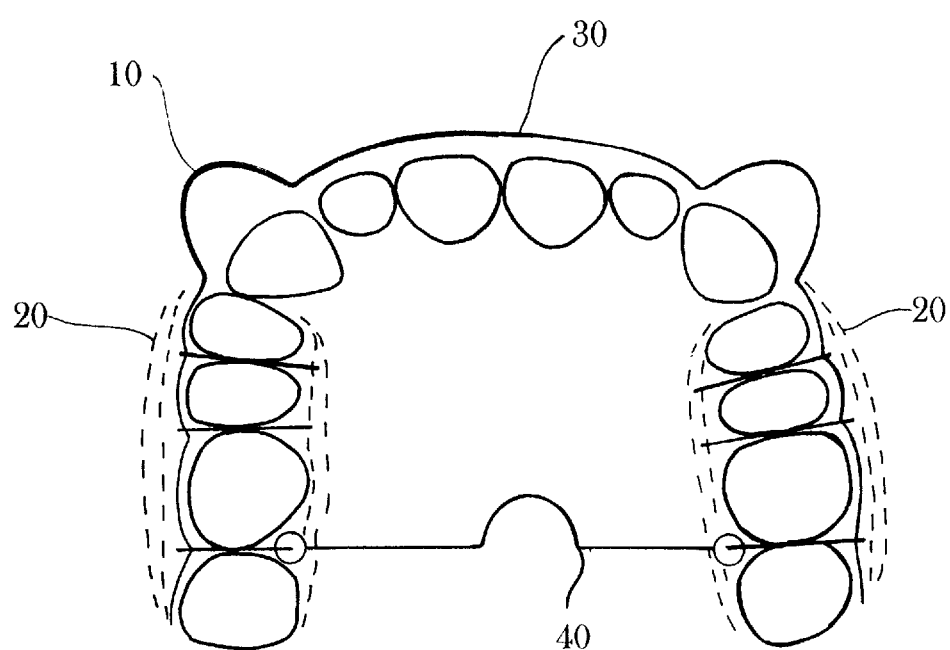

Nasal airways will improve in different ways for different patients. Factors involved include the shape of the dental arch, relative size of the teeth, shape of the maxilla, angulation of maxillary teeth (most important are cuspids, premolars, and first molars), reaching true vertical location of soft-tissue edema, previous surgical procedures, etc. Shaping of the maxilla appears to have the most impact.

The present invention will shape and control the shape of the nasal airway. This will be achieved by expanding the maxilla in a controlled manner by the way it is attached on the posterior teeth. This device moves the teeth to which it is attached, primarily the first and second premolars and first molar and sometimes an additional load on the cuspid. Optionally, the second molar is used most often for stability and placement reference but can be expanded or moved inward when needed by changing the posterior body wire (optional part of nasal airway device) and/or the optional distal extension of anterior body wire.

Construction is done on a model made from an impression by placing two or three ball clasps interproximally into the lingual of the posterior teeth of the maxillary arch. All the clasps are placed tight into inter proximal undercut area for retention of device and to hold lingual plastic. Clasps are between first and second molars, first molar and second premolar. The ball is preferred to be on the lingual gingival line. Sometimes a ball clasp is needed on the mesial of first premolar. The ball clasp ends are bent one to four millimeters depending on the height of the tooth, at a ninety degree angle to just reach the gingiva. The ball clasp area is kept free of plastic to allow for adjusting it. The plastic is also kept out of this area to prevent trapping oral fluids. Optionally, plastic can contact the incisal tip of the lower cuspids. This is to control vertical and prevent intrusion of teeth. The buccal extension of each clasp passes over the contact of the teeth and then is bent into the inter proximal area and then straight up to act as a heat sink and to hold the anterior body wire when soldered. The anterior body wire is extended back to lay in the buccal extension of the clasp and soldered.

Finally, the buccal and lingual of the first molar and the second and first premolars along with wire there is covered by 2 to 5 mm of plastic. The occlusal surface is covered by about 1–2 mm of plastic and is used for strength, retention, and stability.

Now referring to FIG. 1. there is disclosed a preferred embodiment of the present invention 10. The posterior retention segments 20 are connected to one another by the anterior body wire 30. The anterior body wire 30 is connected to the posterior retention segments 20 such as to cause torque in front of said patient's anterior teeth when matingly engaging the posterior teeth of a patient sufficient to cause the separation of said patient's two maxillas. An optional posterior body wire 40 is attached to said pair of posterior retention segments as shown.

When the patient wears the orthopedic appliance the posterior teeth, preferably three, on each of the maxilla's are torqued outward at their roots so that the two maxilla move apart at the front enough to increase nasal air movement. This is due to the interaction between the two maxilla's and the attached teeth.

While a full and complete description of the invention has been set forth it should be understood that modifications can be resorted to without departing from the spirit hereof or the scope of the appended claims.

What is claimed is:

1. An orthopedic appliance, comprising:
   a) a pair of posterior retention segments each able to matingly engage the posterior teeth of a patient and being adapted to be positioned interproximally into the lingual of said posterior teeth of the maxillary arch of said patient;
   b) an anterior body wire connecting said pair of posterior retention segments; and
   c) said anterior body wire being labial of said patient's anterior teeth and having torque labial of said patient's anterior teeth sufficient to cause the separation of said patient's two maxillas.

2. The orthopedic appliance as recited in claim 1 further comprising an orthopedic acceptable plastic covering said posterior retention segment being adapted to matingly engage said posterior teeth of said patient at about the gingiva of said patient.

3. The orthopedic appliance as recited in claim 1 wherein each said pair of posterior retention segments further comprise at least two ball clasps.

4. The orthopedic appliance as recited in claim 3 wherein said ball clasp has ends bent upward towards said patient's gingival line.

5. The orthopedic appliance as recited in claim 1 further comprising a posterior body wire attached to said pair of posterior retention segments.

6. A method of separating a patient's two maxillas, comprising:
   a) providing an orthopedic appliance of claim 1; and
   b) having said patient wear said orthopedic appliance to separate said two maxillas.

7. An orthopedic appliance, consisting essentially of:
   a) a pair of posterior retention segments each able to matingly engage the posterior teeth of a patient and being adapted to be positioned interproximally with clasp between said posterior teeth of the maxillary arch of said patient;
   b) an anterior body wire connecting said pair of posterior retention segments; and
   c) said anterior body wire being labial of said patient's anterior teeth and having torque labial of said patient's anterior teeth sufficient to cause the separation of said patient's two maxillas.

* * * * *